United States Patent [19]

Gainutdinova et al.

[11] Patent Number: 4,935,003
[45] Date of Patent: Jun. 19, 1990

[54] GYNECOLOGICAL ASPIRATION TIP

[76] Inventors: Raisa V. Gainutdinova, ulitsa Spartakovskaya, 80, kv. 15, Kazan; Irina A. Manuilova, ulitsa 1812 goda, 3, kv. 110, Moscow; Vera M. Petrova, ulitsa Frunze, 13a, kv. 2, Kazan; Yakov G. Zhukovsky, ulitsa Krupskoi, 14, kv. 76, Moscow, all of U.S.S.R.

[21] Appl. No.: 271,957
[22] PCT Filed: Jan. 5, 1988
[86] PCT No.: PCT/SU88/00002
  § 371 Date: Sep. 7, 1988
  § 102(e) Date: Sep. 7, 1988
[87] PCT Pub. No.: WO88/04913
  PCT Pub. Date: Jul. 14, 1988

[30] Foreign Application Priority Data

Jan. 8, 1987 [SU] U.S.S.R. ............... 4176523

[51] Int. Cl.⁵ ............................................. A61M 1/00
[52] U.S. Cl. ....................................... 604/27; 664/35; 664/275; 128/758

[58] Field of Search .......... 604/30, 31, 35, 93, 604/275, 902, 27; 433/91-96; 128/758, 759, 799; 606/119, 191, 193

[56] References Cited

U.S. PATENT DOCUMENTS

| | | | |
|---|---|---|---|
| 2,531,730 | 11/1950 | Henderson | 433/91 |
| 3,661,144 | 5/1972 | Jensen et al. | 128/258 |
| 3,965,901 | 6/1976 | Penny et al. | 128/276 |
| 4,451,257 | 5/1984 | Atchley | 604/119 |
| 4,504,266 | 3/1985 | Härle | 604/118 |

Primary Examiner—Jerome L. Kruter
Attorney, Agent, or Firm—Fleit, Jacobson, Cohn, Price, Holman & Stern

[57] ABSTRACT

A gynecological aspiration tip is made as a flexible cylindrical hollow tube (1) having a slot (2) in its wall. The slot (2) communicates with the interior of the tube (1) and is located at a distal end (3) of the tube. The slot (2) is open on the side of a face (4) of the distal and (3) of the tube (1). A proximal end (5) of the tube (1) is adapted to communicate with a source of vacuum.

2 Claims, 1 Drawing Sheet

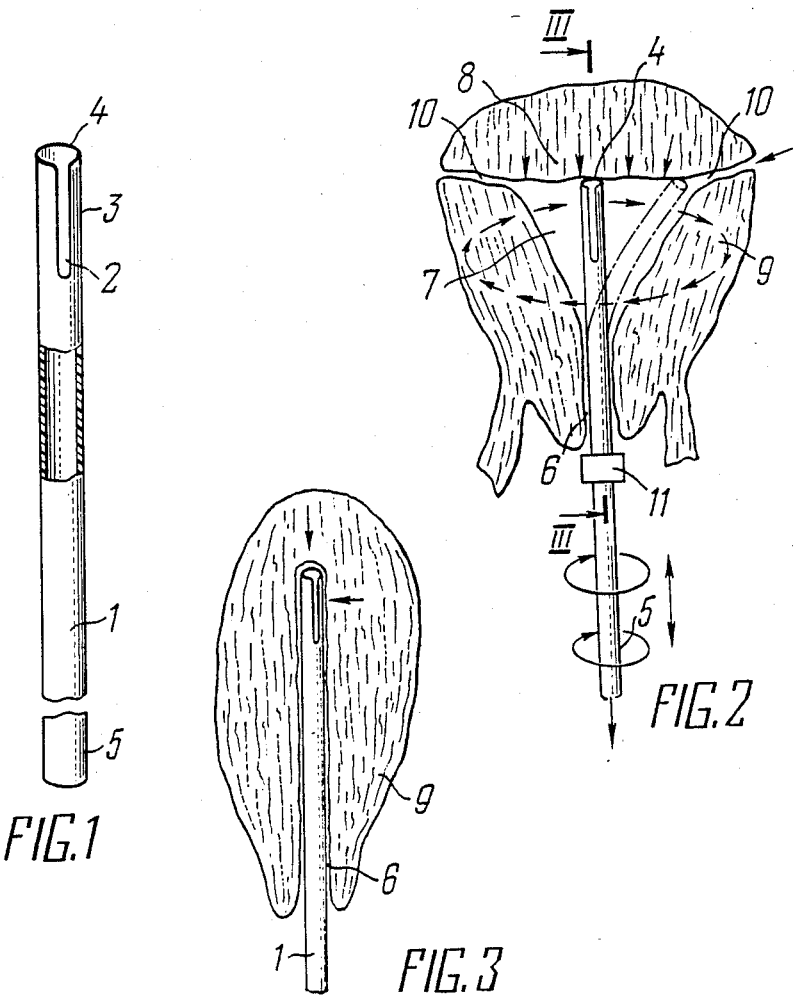

4,935,003

GYNECOLOGICAL ASPIRATION TIP

TECHNICAL FIELD

The present invention relates generally to devices for early-stage abortion and more specifically to a gynecological aspiration tip.

The invention can find application in gynecological practice for early-stage abortion, as well as for aspiration of the contents out of the uterine cavity in cases of various pathological changes of the latter, e.g, in the case of hyperplastic changes in the endometrium, suspicion for endometrial or cervical carcinoma, infertility, or cervical polyps.

The present invention is instrumental in a more complete aspiration of the uterine cavity contents without inflicting any painful syndrome upon the patient.

PRIOR ART

Two types of the state-of-the-art gynecological aspiration tips are heretofore available, i.e., aspiration tips with a scraping (curetting) effect and those operating on the vacuum aspiration principle alone.

In the former case the tip is essentially a cylindrical tube with the distal end closed and two perforations in the lateral walls thereof, a sharp triangular projection being provided above one of the perforations capable of exerting a curetting effect.

The aforediscussed known device, while curetting the uterine walls, inflicts injury upon the nerve endings located in the uterine walls, thus causing subsequent morbid sequels.

In the latter case the tip is likewise shaped as a cylindrical tube with its distal end closed or open and perforations in the lateral walls but devoid of a sharp projection. Such a tip is for extraction of the uterine contents by the pure aspiration method.

However, perforations in the lateral tip walls are liable to get clogged with pieces of mucosa, which stop up the tip and hence cause the surgical procedure to cease, whereas repeated insertion of the tip into the uterine cavity might bring the infection into the latter.

One prior-art aspiration tip (U.S., A, 3,965,901) is known to be a flexible cylindrical tube having an open face end and a T-slot in the lateral wall at the distal end thereof, said slot communicating with the tube interior. The proximal end of the tube is adapted to communicate with a source of vacuum.

The aforesaid known device is featured by the fact that, upon introduction of the tip into the uterine cavity and establishing a subatmospheric pressure therein, the uterine mucosa (endometrium) that has changed due to pregnancy or a pathological process, makes it way through the slot of the tip into its interior and further into the receptacle for aspirate collection.

However, in the case of aspiration with the known tip the slot might get clogged and stopped up with large pieces of the endometrium, which results in discontinuation of the surgical procedure, compels one to withdraw the tip from the uterine cavity and clean the clogged slot. Repeated introduction of the tip into the uterine cavity might contribute to its infecting with the secondary morbid complications.

The aforesaid known device is also characterized by the fact that a contact between the tip slot and the endometrium is established during aspiration at a preset vacuum, whereby painful sensations may occur owing to an adequately large contact area.

DISCLOSURE OF THE INVENTION

The invention has for its object to provide a gynecological aspiration tip whose construction arrangement makes it possible to perform more perfect extraction of the gravidic or pathologically changed endometrium without forced interruptions of the surgical procedure, thus preventing the uterus from being infected.

The aforesaid object is accomplished due to the fact that in a gynecological aspiration tip shaped as a flexible cylindrical hollow tube having a slot in its wall, said slot communicating with the hollow interior of the tube and located at the tube distal end, while the proximal tube end is adapted to communicate with a source of vacuum, according to the invention, the slot is open at the face of the tube distal end.

Provision of the tip with such a slot ensures the maximum area of contact of the slot with the uterine walls, which makes it possible to carry out aspiration involving complete extraction of the endometrium simultaneously from the uterine fundus and lateral walls.

Furthermore, such an arrangement of the slot makes it possible to pass the tip through the cervical canal of the uterus without preliminarily dilating the latter, since elastic lateral walls of the cervical canal compress the distal end of the tip, thus reducing the circumferential length of the end opening by the slot width and hence decreasing the outside diameter of said opening.

It is desirable that the ratio between the slot width and its length be from about 1:6 to 1:10 and the slot width be from about one-third to about one-half the tube outside diameter.

Such slot dimensions provide for a complete extraction of the endometrium while no painful sensations are felt by the patient at a preset degree of vacuum.

An increase in the slot dimensions leads to a slot dimensions cause clogging of the slot with the particles of the endometrium.

It is expedient that the slot should mate the face of the tube distal end through its open end.

Such an arrangement of the slot edges renders the tip atraumatic.

SUMMARY OF THE DRAWINGS

In what follows the invention will become apparent from a consideration of a specific embodiment thereof with reference to the accompanying drawings, wherein:

FIG. 1 is a general diagrammatic view of a gynecological aspiration tip, according to the invention;

FIG. 2 is a tip, according to the invention, when introduced into the uterine cavity through the cervical canal; and FIG. 3 is a view of the section III—III in FIG. 2 at the instant of completion of the surgical procedure, showing the tip of the invention purposely not slotted.

PREFERRED EMBODIMENT OF THE INVENTION

The gynecological aspiration tip is shaped as a flexible cylindrical tube 1 (FIG. 1). A slot 2 is provided on its wall, said slot communicating with the interior of the tube 1 and being located at a distal end 3 of the tube 1.

The slot 2 is open on the side of a face 4 of the distal end 3 of the tube 1 and mates the face 4.

It is due to mating of the slot 2 and the end opening that a more complete extraction of the gravidic endometrium from the lateral angles of the uterus and elimination of the painful syndrome are provided.

Provided is made for a proximal end 5 of the tube 1 to communicate with a source of vacuum.

FIG. 2 illustrates the tip while in the course of surgery.

The tip is introduced into a uterine cavity 7 without dilating a cervical canal 6 until the face end 4 contacts a uterine fundus 8, lateral walls 9 and lateral angles 10 of the uterus.

A restrictor 11 is provided on the tube 1 whose location depends on the depth of the uterine cavity 7 which is to be found by probing the uterus beforehand. The restrictor 11 is set on the tube 1 at such a distance from its distal end 3 that is equal to the depth of the uterine cavity 7, whereby the tube may be introduced only for that depth and hence makes it possible to avoid injury to the uterus.

FIG. 3 illustrates the completing stage of surgery showing the tip tightly encompassed by the walls 9 of the uterus and the walls of the cervical canal 6.

The gynecological aspiration tip of the present invention is applied as follows.

The tip (FIG. 2) is introduced into the uterine cavity 7 without dilating the cervical canal 6 until the face end 4 contacts the uterine fundus 8. The proximal end 5 of the tip is connected to the source of vacuum, a subatmospheric pressure is fed thereto and the tip is rotated round its axis while inclining it first towards one of the lateral angles 10 of the uterus, then towards the other and imparting reciprocating motion thereto.

During surgery that portion of the tip which is located in the uterine cavity 7 gets heated, with the result that it becomes more elastic and deflects towards the lateral walls 9 of the uterus, which renders the surgical procedure more perfect.

The ratio of the slot width to its length equals approximately 1:6 for the non-para, and 1:10 for the uni- or multipara patients. The ratio between the slot width and its outside diameter equals predominantly 1:3 for the non-para, and largely 1:2 for the uni- or multipara patients.

Thus, it is due to the embodiment of the gynecological aspiration tip as described before that one can avoid clogging of the slot with the particles of the endometrium, which makes it possible to cut down the operating time, prevent infection of the uterine cavity, while the optimal ratios between the slot width, length and outside diameter make it possible to avoid painful syndrome in the patient.

INDUSTRIAL APPLICABILITY

The present invention can find application in gynecological practice for early stage abortion as well as for biopsy of endometrium.

What is claimed is:

1. A gynecological aspiration tip comprising
a flexible, cylindrical hollow tube means having an open distal end and a proximal end for extraction of gravidic or pathologically changed endometrium simultaneously from the uterine fundus and lateral walls,
a single slot means defined by a side wall of said tube means extending from said open distal end along said tube means toward said proximal end and said slot means communicating with the interior of the tube means, said distal end including said slot means being compressible to reduce the circumferential length during passage through the cervical canal, said proximal end of the tube means being adapted to communicate with a source of vacuum.

2. A gynecological aspiration tip as claimed in claim 1, wherein a ratio of a width of the slot means to its length ranges within about 1:6 to about 1:10, and the width of the slot means equals from about one-third to about one-half the outside diameter of the flexible cylindrical hollow tube means.

* * * * *